United States Patent
Schwartz

(10) Patent No.: US 8,978,666 B2
(45) Date of Patent: Mar. 17, 2015

(54) METHOD FOR PROVIDING MAXIMUM MALODOR AND IRRITATION CONTROL

(75) Inventor: James Robert Schwartz, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 360 days.

(21) Appl. No.: 13/028,890

(22) Filed: Feb. 16, 2011

(65) Prior Publication Data

US 2011/0197907 A1 Aug. 18, 2011

Related U.S. Application Data

(60) Provisional application No. 61/305,132, filed on Feb. 16, 2010.

(51) Int. Cl.
*A45D 27/00* (2006.01)
*A61Q 9/02* (2006.01)
*A61K 8/27* (2006.01)
*A61K 8/49* (2006.01)

(52) U.S. Cl.
CPC ... *A61Q 9/02* (2013.01); *A61K 8/27* (2013.01); *A61K 8/4933* (2013.01); *A61K 2800/58* (2013.01)
USPC ........................................... 132/200; 424/405

(58) Field of Classification Search
None
See application file for complete search history.

(56) References Cited

U.S. PATENT DOCUMENTS

| | | | |
|---|---|---|---|
| 3,235,455 A | 2/1966 | Judge et al. | |
| 3,281,366 A | 10/1966 | Judge et al. | |
| 3,412,033 A | 11/1968 | Karsten et al. | |
| 3,725,547 A | 4/1973 | Kooistra | |
| 4,345,080 A | 8/1982 | Bolich, Jr. | |
| 4,379,753 A | 4/1983 | Bolich, Jr. | |
| 4,565,693 A | 1/1986 | Marschner | |
| 4,708,863 A | 11/1987 | Bews et al. | |
| 4,714,563 A | 12/1987 | Kajs et al. | |
| 5,037,818 A | 8/1991 | Sime | |
| 5,104,645 A | 4/1992 | Cardin et al. | |
| 5,540,860 A | 7/1996 | Hosseini et al. | |
| 5,573,699 A | 11/1996 | Jones et al. | |
| 5,612,301 A | 3/1997 | Inman | |
| 5,886,031 A | 3/1999 | Shin et al. | |
| 6,015,547 A | 1/2000 | Yam | |
| 6,017,562 A | 1/2000 | Kaufman et al. | |
| 6,017,936 A | 1/2000 | Polson et al. | |
| 6,096,297 A | 8/2000 | Jones et al. | |
| 6,162,446 A | 12/2000 | Hani et al. | |
| 6,242,007 B1 | 6/2001 | Mohseni et al. | |
| 6,277,360 B1 | 8/2001 | Carew et al. | |
| 6,432,432 B1 | 8/2002 | Mohseni et al. | |
| 6,451,300 B1 | 9/2002 | Dunlop et al. | |
| 6,465,015 B1 | 10/2002 | Mohseni et al. | |
| 6,649,155 B1 | 11/2003 | Dunlop et al. | |
| 6,673,756 B2 | 1/2004 | Sonnenberg et al. | |
| 6,682,724 B2 | 1/2004 | Mohseni et al. | |
| 6,774,096 B1 | 8/2004 | Paye | |
| 6,887,859 B2 | 5/2005 | Clapp et al. | |
| 6,974,569 B2 | 12/2005 | Dunlop et al. | |
| 7,026,308 B1* | 4/2006 | Gavin et al. | 514/188 |
| 7,381,415 B2 | 6/2008 | Yokoyama et al. | |
| 7,544,367 B2 | 6/2009 | Mohseni et al. | |
| 7,674,785 B2 | 3/2010 | Gavin et al. | |
| 8,491,877 B2 | 7/2013 | Schwartz et al. | |
| 8,685,908 B2 | 4/2014 | Smith, III et al. | |
| 2003/0104021 A1* | 6/2003 | Burnier | 424/401 |
| 2004/0161435 A1 | 8/2004 | Gupta | |
| 2004/0191331 A1 | 9/2004 | Schwartz et al. | |
| 2004/0213751 A1 | 10/2004 | Schwartz et al. | |
| 2005/0118276 A1 | 6/2005 | Lei et al. | |
| 2005/0202984 A1 | 9/2005 | Schwartz et al. | |
| 2005/0244352 A1 | 11/2005 | Lemoine et al. | |
| 2005/0271595 A1 | 12/2005 | Brown | |
| 2006/0024381 A1 | 2/2006 | Schwartz et al. | |
| 2007/0009463 A1 | 1/2007 | Niebauer et al. | |
| 2007/0009472 A1 | 1/2007 | Niebauer et al. | |
| 2007/0128147 A1 | 6/2007 | Schwartz et al. | |
| 2007/0190177 A1 | 8/2007 | Kling et al. | |
| 2008/0138441 A1 | 6/2008 | Schwartz et al. | |
| 2008/0138442 A1 | 6/2008 | Johnson et al. | |
| 2008/0160093 A1 | 7/2008 | Schwartz et al. | |
| 2008/0206355 A1 | 8/2008 | Schwartz et al. | |
| 2008/0220031 A1* | 9/2008 | Wunsch et al. | 424/401 |
| 2008/0249136 A1 | 10/2008 | Annis et al. | |
| 2011/0197906 A1 | 8/2011 | Schwartz | |
| 2011/0200649 A1 | 8/2011 | Schwartz | |

(Continued)

FOREIGN PATENT DOCUMENTS

DE 19537509 A1 4/1997
EP 0 034 385 A2 8/1981

(Continued)

OTHER PUBLICATIONS

International Search Report PCT/US2011/025024 dated Mar. 16, 2012, 14 pages.
Shannon Cotton, How to Shave Armpits Properly, Jul. 25, 2010, URL:http://www.livestrong.com/article/184030, retrieved Jan. 25, 2012, 6 pages.
Mintel GNPD Database, Soft Shower Shave & Go, Record ID: 858404, product description and ingredients, Feb. 2008, 2 pages.
Raphael Warren et al., Attenuation of Surfactant-Induced Interleukin 1a Expression by Zinc Pyrithione, Exogenous Dermatology Clinical and Experimental Studies, vol. 2, No. 1, Jan. 2003, pp. 23-27, 5 pages.
Is Pyrithione Zinc good for persistant razor irritation, URL:http://www.askmehelpdesk.com, Mar. 25, 2009, 3 pages.
How to Avoid Armpit Irritation, URL:http://thebeautybrains.com, Jul. 29, 2007, 7 pages.

(Continued)

*Primary Examiner* — David J Blanchard
*Assistant Examiner* — Daniel F Coughlin

(57) ABSTRACT

A method for reducing irritation on an intimate area comprising: applying an intimate cleansing product to the intimate area; rinsing the intimate cleansing product from the intimate area; applying a shave preparation to the intimate area; shaving the intimate area; wherein the intimate cleansing product comprises a malodor active.

6 Claims, No Drawings

(56) References Cited

U.S. PATENT DOCUMENTS

| | | |
|---|---|---|
| 2011/0200650 A1 | 8/2011 | Schwartz |
| 2011/0201588 A1 | 8/2011 | Schwartz |
| 2012/0039966 A1 | 2/2012 | Capretta et al. |
| 2012/0103151 A1 | 5/2012 | Jones et al. |
| 2012/0195944 A9 | 8/2012 | Capretta et al. |
| 2012/0216408 A1 | 8/2012 | Cook et al. |
| 2012/0219610 A1 | 8/2012 | Smith, III et al. |
| 2012/0246851 A1 | 10/2012 | Smith, III et al. |
| 2012/0324736 A1 | 12/2012 | Eagleton |
| 2013/0042482 A1 | 2/2013 | Bradford et al. |
| 2013/0045248 A1 | 2/2013 | Coffindaffer et al. |
| 2013/0045255 A1 | 2/2013 | Smith, III et al. |
| 2013/0045256 A1 | 2/2013 | Schwartz |
| 2013/0045257 A1 | 2/2013 | Alwattari et al. |
| 2013/0045263 A1 | 2/2013 | Smith, III et al. |
| 2013/0045284 A1 | 2/2013 | Stella |
| 2013/0045285 A1 | 2/2013 | Stella et al. |
| 2013/0045907 A1 | 2/2013 | Lanzalaco et al. |
| 2013/0045961 A1 | 2/2013 | Smith, III et al. |
| 2013/0048005 A1 | 2/2013 | Smith, III et al. |
| 2013/0205959 A1 | 8/2013 | Jones et al. |
| 2013/0280200 A1 | 10/2013 | Schwartz |
| 2013/0303503 A1 | 11/2013 | Smith, III et al. |

FOREIGN PATENT DOCUMENTS

| | | | |
|---|---|---|---|
| EP | 0 093 541 | A2 | 11/1983 |
| EP | 0 158 481 | A2 | 10/1985 |
| EP | 0 196 824 | A2 | 10/1986 |
| EP | 0 217 635 | A2 | 4/1987 |
| EP | 285388 | A2 | 10/1988 |
| EP | 468564 | A2 | 1/1992 |
| JP | 2006176675 | A | 7/2006 |
| WO | 9414408 | A1 | 7/1994 |
| WO | 9414409 | A1 | 7/1994 |
| WO | 99/66886 | A1 | 12/1999 |
| WO | 0035413 | A1 | 6/2000 |
| WO | 02/00178 | A1 | 1/2002 |
| WO | 2006110386 | A1 | 10/2006 |

OTHER PUBLICATIONS

Calming Red, Irritated Underarms, URL:http://www.dailyglow.com, Aug. 15, 2011, 6 pages.

Mintel GNPD Database, Shaving Mousse, Record ID: 735257, product description and ingredients, Jul. 2007, 2 pages.

Photographs of DermaZinc Zinc Therapy Bar by Dermalogix Partners, Inc. purchased from DERMAdoctor.com via Amazon Marketplace on May 23, 2011 and believed to have been on the market in the US at least a year before the filing date of this application.

Photographs of ZNP Bar by Stiefel Laboratories, Inc. believed to have been on the market in the US at least a year before the filing date of this application.

U.S. Appl. No. 13/856,457, filed Apr. 4, 2013 Smith, III et al.

U.S. Appl. No. 14/208,821, filed May 9, 2013, Jiang et al.

U.S. Appl. No. 14/255,714, filed Apr. 17, 2014, Jiang et al.

\* cited by examiner

METHOD FOR PROVIDING MAXIMUM MALODOR AND IRRITATION CONTROL

CROSS REFERENCE TO RELATED APPLICATION

This application claims the benefit of U.S. Provisional Application No. 61/305,132, filed Feb. 16, 2010.

FIELD OF THE INVENTION

The present invention is related to a line of consumer products for reducing malodor and shave related irritation.

BACKGROUND OF THE INVENTION

Shaving hairs from the skin is a well-known grooming activity. One consistent complaint involved with shaving is the irritation that is caused by performing the shaving activity. Attempts to overcome this problem include providing additional lubricants, thickeners, surfactants, and the like. Even as many of these systems provide lubrication and/or a smooth shave, skin irritation remains a problem.

On the face, after-shave materials provide some relief from irritation, but often these materials are not suitable for intimate areas. Moreover, there are the added complexities within these intimate areas that make them more suitable for microbial infection. Moreover, as skin irritation indicates damage to the skin, the skin is left even more susceptible to microbial infection, which could result in additional malodor. A number of approaches to reduce irritation have been attempted, but have not resulted in satisfactory results. Thus, there is a need to treat the irritation of the skin as well as treat the skin for antimicrobials.

SUMMARY OF THE INVENTION

The present invention relates to a method for reducing irritation on an intimate area comprising: applying an intimate cleansing product to the intimate area; rinsing the intimate cleansing product from the intimate area; applying a shave preparation to the intimate area; shaving the intimate area; wherein the intimate cleansing product comprises a malodor active.

DETAILED DESCRIPTION OF THE INVENTION

While the specification concludes with the claims particularly pointing and distinctly claiming the invention, it is believed that the present invention will be better understood from the following description.

As used herein, "comprising" means that other steps and/or ingredients can be added. This term encompasses the terms "consisting of" and "consisting essentially of". The phrase "consisting essentially of" means that the invention may include additional steps and/or ingredients, but only if the additional ingredients and/or steps do not materially alter the basic and novel characteristics of the claimed invention or methods.

All percentages, parts and ratios are based upon the total weight of the topical compositions of the present invention and all measurements made are at 25° C., unless otherwise specified. All such weights as they pertain to listed ingredients are based on the active level and, therefore; do not include carriers or by-products that may be included in commercially available materials, unless otherwise specified.

The present invention involves a method for reducing irritation on an intimate area comprising: applying an intimate cleansing product to the intimate area; rinsing the intimate cleansing product from the intimate area; applying a shave preparation to the intimate area; shaving the intimate area; wherein the intimate cleansing product comprises a malodor active. Optionally, an antiperspirant or deodorant can be applied for additional malodor/wetness protection.

Intimate Cleansing Product

The intimate cleansing product described herein may include a variety of personal care products including, but not limited to, body wash, body sprays, lotions, creams, and the like. Depending on the form, the intimate cleansing product may be applied by direct application, placement on a washing implement, spraying, and the like. Washing implements include sponges, towels, bath puffs, brushes, and the like. Without wishing to be bound by theory, it is believed that a washing implement provides an additional scrubbing mechanism allowing further penetration of the intimate cleansing product into the pores and/or follicles of the skin.

The intimate cleansing product is suitable for application to an intimate area. Intimate areas of the present invention include the underarm, crotch, feet, intergluteal cleft, and the like. In one embodiment, the intimate cleansing product of this invention is utilized on the underarm. The application of the intimate cleansing product may take place during a shower or while taking a bath. It is also contemplated that the application of the intimate cleansing product may take place outside of the shower or bath, by applying and rinsing utilizing a wash sink It is contemplated that the intimate cleansing product of the present invention is removed after application. Typical removing methods including rinsing, in either the shower or bath, and/or utilizing a washing implement. One of ordinary skill is readily capable of determining an effective method of removing the intimate cleansing product from an intimate area.

Shave Preparation

The shave preparation of the present invention includes both non-aerosol and aerosol based shave preparations. The shave preparations of the present invention assist a razor or blade in removing hair from the skin. The shave preparation provides a layer between the razor and the skin that improves the shaving experience by increasing the comfort of the shave. This mechanism is facilitated by adding thickeners, lubricants, and the like.

The shave preparations are suitable for application to an intimate area. In one embodiment, the shave preparation of this invention is utilized on the underarm. The application of the shave preparation may take place during a shower or while taking a bath. It is also contemplated that the application of the shave preparation may take place outside of the shower or bath, by applying and rinsing utilizing a wash sink It is contemplated that the shave preparation of the present invention is removed after application. Typical removing methods including rinsing, in either the shower or bath, and/or utilizing a washing implement. One of ordinary skill is readily capable of determining an effective method of removing the intimate cleansing product from an intimate area.

Malodor Active

In one embodiment, the intimate cleansing product and/or the shave preparation comprises a malodor active. The malodor active of the present invention is capable of providing an antimicrobial benefit. Such malodor actives are capable of destroying microbes, preventing the development of microbes or preventing the pathogenic action of microbes. A safe and effective amount of a malodor active may be added to the intimate cleansing product, at from about 0.001% to about 10%, or from about 0.01% to about 5%, or from about 0.05% to about 2%, or from about 0.1% to about 1%, or from about 0.3% to about 0.7%, or about 0.5% by weight of, e.g. the cleansing product.

Examples of malodor actives include β-lactam drugs, quinolone drugs, ciprofloxacin, norfloxacin, tetracycline, erythromycin, amikacin, 2,4,4'-trichloro-2'-hydroxy diphenyl ether, 3,4,4'-trichlorobanilide, phenoxyethanol, phenoxy propanol, phenoxyisopropanol, doxycycline, capreomycin, chlorhexidine, chlortetracycline, oxytetracycline, clindamycin, ethambutol, hexamidine isethionate, metronidazole, pentamidine, gentamicin, kanamycin, lineomycin, methacycline, methenamine, minocycline, neomycin, netilmicin, paromomycin, streptomycin, tobramycin, miconazole, tetracycline hydrochloride, erythromycin, zinc erythromycin, erythromycin estolate, erythromycin stearate, amikacin sulfate, doxycycline hydrochloride, capreomycin sulfate, chlorhexidine gluconate, chlorhexidine hydrochloride, chlortetracycline hydrochloride, oxytetracycline hydrochloride, clindamycin hydrochloride, ethambutol hydrochloride, metronidazole hydrochloride, pentamidine hydrochloride, gentamicin sulfate, kanamycin sulfate, lineomycin hydrochloride, methacycline hydrochloride, methenamine hippurate, methenamine mandelate, minocycline hydrochloride, neomycin sulfate, netilmicin sulfate, paromomycin sulfate, streptomycin sulfate, tobramycin sulfate, miconazole hydrochloride, ketaconazole, amanfadine hydrochloride, amanfadine sulfate, octopirox, parachlorometa xylenol, nystatin, tolnaftate, zinc pyrithione and clotrimazole.

Without wishing to be bound by theory, it is believed that the compositions of the present invention surprisingly provide an antimicrobial benefit and reduce irritation. It is believed that zinc pyrithione, when added to these compositions, provides the synergistic benefit of reduced irritation, while providing an antimicrobial benefit. It is this unique combination of benefits provided by these compositions that result in an improved shaving experience.

Zinc Salt

The intimate cleansing product and/or the shave preparation of the present invention optionally includes an effective amount of a zinc salt. Preferred embodiments of the present invention include an effective amount of a zinc salt having an aqueous solubility within the composition of less than about 25%, by weight, at 25° C., more preferably less than about 20%; more preferably less than about 15%. Preferred embodiments of the present invention include from 0.001% to 10% of a zinc salt; more preferably from 0.01% to 5%; more preferably still from 0.1% to 3%.

In a preferred embodiment, the zinc salt has an average particle size of from 100 nm to 30 μm.

Examples of zinc salts useful in certain embodiments of the present invention include the following: Zinc aluminate, Zinc carbonate, Zinc oxide and materials containing zinc oxide (i.e., calamine), Zinc phosphates (i.e., orthophosphate and pyrophosphate), Zinc selenide, Zinc sulfide, Zinc silicates (i.e., ortho- and meta-zinc silicates), Zinc silicofluoride, Zinc Borate, Zinc hydroxide and hydroxy sulfate, zinc-containing layered materials and combinations thereof.

In embodiments having an anti-irritation agent and a zinc salt, the ratio of zinc salt to anti-irritation agent is preferably from 5:100 to 5:1; more preferably from about 2:10 to 3:1; more preferably still from 1:2 to 2:1.

Antiperspirant/Deodorant Compositions

Optionally, the antiperspirant and deodorant substances for use with the intimate cleansing product of the present invention are compositions which are intended for topical application to the underarm or other suitable areas of the skin. The terms "antiperspirant active" and "deodorant active" specifically refers to topical materials which can prevent or eliminate malodors and/or perspiration wetness.

Antiperspirant Active

The antiperspirant compositions for use in the present invention comprise antiperspirant active suitable for application to human skin. The antiperspirant active may be solubilized in the antiperspirant compositions or may be suspended as an undissolved or precipitated solid. The concentration of the antiperspirant active in the antiperspirant compositions should be sufficient to provide the desired odor and wetness control from the antiperspirant composition selected.

The antiperspirant compositions of the present invention can be formulated as any known or otherwise effective product form for providing topical application of antiperspirant or deodorant active to the desired area of the skin. Non-limiting examples of such product forms include liquids (e.g., aerosols, pump sprays, roll-ons), solids (e.g., gel solids, invisible solids, wax solid sticks), semi-solids (e.g. creams, soft solids, lotions), and the like. For example, the antiperspirant compositions of the present invention may be semi-solids or solids.

The antiperspirant products are generally stored in and dispensed from a suitable package or applicator device. For example, the package or applicator device may be a cream dispenser with perforated application domes, etc. These packages should be sufficiently closed to prevent excessive loss of volatiles prior to application.

The antiperspirant compositions described herein comprise antiperspirant active at concentrations of from about 0.5% to about 60%, preferably from about 0.5% to about 50%, more preferably from about 5% to about 35%, by weight of the selected antiperspirant composition. All such weight percentages are calculated on an anhydrous metal salt basis exclusive of water and any complexing agents such as glycine, glycine salts, or other complexing agents.

The antiperspirant active for use in the antiperspirant compositions described herein include any compound, composition or other material having antiperspirant activity. Preferred antiperspirant actives include the astringent metallic salts, especially the inorganic and organic salts of aluminum, zirconium and zinc, as well as mixtures thereof. Particularly preferred are the aluminum and zirconium salts, such as aluminum halides, aluminum hydroxyhalides, zirconyl oxyhalides, zirconyl hydroxyhalides, and mixtures thereof.

The antiperspirant active may be formulated as particulate solids in the form of dispersed solid particles having a preferred average particle size or diameter of less than about 100 μm, more preferably from about 2 μm to about 50 μm, even more preferably from about 0.4 μm to about 40 μm.

The antiperspirant compositions described herein may comprise solubilized antiperspirant active, preferably solubilized antiperspirant active in an anhydrous system. The concentration of solubilized antiperspirant active in the antiperspirant compositions preferably ranges from about 0.1% to 35%/, more preferably from about 0.5% to about 25%, even more preferably from about 1% to about 17%, even more preferably from about 6% to about 17%, by weight of the selected antiperspirant composition (weight percentages calculated on an anhydrous metal salt basis exclusive of water and any complexing agents such as glycine, glycine salts, or other complexing agents).

Deodorant Active

The deodorant compositions for use in the applicator of the present invention comprise deodorant active at concentrations ranging from about 0.001% to about 50%, preferably from about 0.01% to about 20%, more preferably from about 0.1% to about 10%, even more preferably from about 0.1% to about 5%, by weight of the selected deodorant composition. These deodorant actives can include any known or otherwise safe and effective deodorant active suitable for topical application to human skin Deodorant actives suitable for use in the deodorant compositions described herein include any topical material that is known for or is otherwise effective in preventing or eliminating malodor associated with perspiration. These deodorant actives are typically antimicrobial agents (e.g., bacteriocides, fungicides), malodor-absorbing material, or combinations thereof.

Preferred deodorant actives are antimicrobial agents, non-limiting examples of which include cetyl-trimethylammonium bromide, cetyl pyridinium chloride, benzethonium chloride, diisobutyl phenoxy ethoxy ethyl dimethyl benzyl ammonium chloride, sodium N-lauryl sarcosine, sodium N-palmethyl sarcosine, lauroyl sarcosine, N-myristoyl glycine, potassium N-lauryl sarcosine, trimethyl ammonium chloride, sodium aluminum chlorohydroxy lactate, triethyl citrate, tricetylmethyl ammonium chloride, 2,4,4'-trichlorio-2'-hydroxy diphenyl ether (triclosan), 3,4,4'-trichlorocarbanilide (triclocarban), diaminoalkyl amides such as L-lysine hexadecyl amide, heavy metal salts of citrate, salicylate, and piroctose, especially zinc salts, and acids thereof, heavy metal salts of pyrithione, especially zinc pyrithione, zinc phenolsulfate, farnesol, and combinations thereof.

Other deodorant actives include odor-absorbing materials such as carbonate and bicarbonate salts, including alkali metal carbonates and bicarbonates, ammonium and tetraalkylammonium. Preferred are sodium and potassium salts of such odor-absorbing materials.

The deodorant compositions of the present invention can be formulated as any known or otherwise effective product form for providing topical application of antiperspirant or deodorant active to the desired area of the skin. Non-limiting examples of such product forms include liquids (e.g., aerosols, pump sprays, roll-ons), solids (e.g., gel solids, invisible solids, wax solid sticks), semi-solids (e.g. creams, soft solids, lotions), and the like. For example, the antiperspirant compositions of the present invention may be semi-solids or solids.

The deodorant products are generally stored in and dispensed from a suitable package or applicator device. For example, the package or applicator device may be a cream dispenser with perforated application domes, etc. These packages should be sufficiently closed to prevent excessive loss of volatiles prior to application.

Method of Use

There are a number of ways that the intimate cleansing product and shave preparation are contemplated for use. In one embodiment, it is contemplated that the intimate cleansing product is applied and utilized directly for shaving. As such, the single composition provides an anti-irritation benefit and an anti-microbial benefit, while being suitable for use in removing hair. As such, the intimate cleansing product, in this embodiment, includes a malodor active. After the shaving step is completed, it is preferred to engage in a rinsing step of the intimate area to remove any remaining intimate cleansing product and/or hair from the shaving step.

It is also contemplated to apply the intimate cleansing product, rinse the intimate cleansing product, and apply the shave preparation. In this embodiment, the shaving step occurs with the shaving preparation on the intimate area. Importantly, the malodor active can be included in the intimate cleansing product, the shave preparation, or the combination. After the application of the shaving preparation, the shaving step begins. After the shaving step is completed, it is preferred to engage in a rinsing step of the intimate area to remove any remaining intimate cleansing product and/or hair from the shaving step.

It is contemplated that the intimate cleansing product and/or shave preparation will be used in combination with an antiperspirant or deodorant. For example, after the intimate cleansing product is applied and rinsed, the antiperspirant or deodorant is applied within an hour of the completion of the shower. It is also contemplated that a drying step may occur between the rinsing step and the application step of the antiperspirant or deodorant. Such drying step can be accomplished by air drying (either hot air or room-temperature air) or by drying with a towel or alternate substrate. One of ordinary skill would readily know mechanisms for drying an intimate area.

Further improved efficacy can be accomplished by performing this invention before a sleep cycle, though use after a sleep cycle is also contemplated. Generally, a sleep cycle includes a rest period of time of at least about 1 hour, at least about 2 hours, at least about 4 hours or at least about 8 hours. Typically, the sleep cycle begins after sunset but before sunrise. However, it is contemplated that individuals may utilize non-traditional sleep cycles.

Without being limited to the above treatment regimens, the present inventors have found that such treatment regimens may help to treat hyperhidrosis by achieving effective antiperspirant reduction or inhibition over an extended period.

Co-Packaging

The products of the present invention may be packaged individually in separate containers or they may be packaged together in a unitary form to be sold and bought together. Written and/or graphic instructions may be included in the separate packages or in the unitary packages to instruct a consumer when and how to use the product. Additionally, the product or products may be packaged in a secondary package wherein an outer container embodies the product disclosed therein.

It should be understood that every maximum numerical limitation given throughout this specification includes every lower numerical limitation, as if such lower numerical limitations were expressly written herein. Every minimum numerical limitation given throughout this specification includes every higher numerical limitation, as if such higher numerical limitations were expressly written herein. Every numerical range given throughout this specification includes every narrower numerical range that falls within such broader numerical range, as if such narrower numerical ranges were all expressly written herein.

All parts, ratios, and percentages herein, in the Specification, Examples, and Claims, are by weight and all numerical limits are used with the normal degree of accuracy afforded by the art, unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited herein are, in the relevant part, incorporated herein by reference; the citation of any document is not to be construed as an admission that it is prior art with respect to the present invention. To the extent that any meaning or definition of a term or in this written document conflicts with any meaning or definition in a document incorporated by reference, the meaning or definition assigned to the term in this written document shall govern.

Except as otherwise noted, the articles "a", "an", and "the" mean "one or more".

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for reducing irritation on an intimate area comprising:
   applying an intimate cleansing product to the intimate area;
   rinsing the intimate cleansing product from the intimate area;
   applying a shave preparation to the intimate area, wherein the shave preparation comprises zinc pyrithione as a malodor active; and
   shaving the intimate area.

2. The method of claim 1, wherein the zinc pyrithione is present at from about 0.001% to about 10% by weight of the shave preparation.

3. The method of claim 1, wherein the shave preparation further comprises zinc oxide.

4. The method of claim 3, wherein the zinc salt is present at from about 0.001% to 10% by weight of the shave preparation.

5. A method for reducing irritation on an intimate area comprising:
   applying an intimate cleansing product to the intimate area, wherein the intimate cleansing product comprises zinc pyrithione as a first malodor active;
   rinsing the intimate cleansing product from the intimate area;
   applying a shave preparation to the intimate area, wherein the shave preparation comprises a second malodor active; and
   shaving the intimate area.

6. The method of claim 5, wherein the intimate area is the underarm.

* * * * *